(12) United States Patent
Lawton et al.

(10) Patent No.: US 7,445,788 B2
(45) Date of Patent: Nov. 4, 2008

(54) **COMPOSITIONS AND METHODS FOR DETECTION OF *EHRLICHIA CANIS* AND *EHRLICHIA CHAFFEENSIS* ANTIBODIES**

(75) Inventors: Robert Lawton, Gorham, ME (US); Thomas Patrick O'Connor, Jr., Westbrook, ME (US); Barbara Ann Bartol, Gorham, ME (US); Paul Scott MacHenry, Portland, ME (US)

(73) Assignee: IDEXX Laboratories, Inc., Westbrook, MA (US)

( * ) Notice: Subject to any disclaimer, the term of this patent is extended or adjusted under 35 U.S.C. 154(b) by 0 days.

(21) Appl. No.: 11/503,817

(22) Filed: Aug. 14, 2006

(65) Prior Publication Data

US 2007/0020733 A1    Jan. 25, 2007

Related U.S. Application Data

(60) Continuation of application No. 10/054,647, filed on Jan. 22, 2002, now abandoned, which is a division of application No. 09/765,739, filed on Jan. 18, 2001, now Pat. No. 7,087,372, which is a continuation of application No. PCT/US02/01395, filed on Jan. 16, 2002.

(51) Int. Cl.
*A61A 39/02* (2006.01)
*A61A 39/00* (2006.01)
*A61K 38/00* (2006.01)
*A01N 37/18* (2006.01)

(52) U.S. Cl. ............... 424/234.1; 424/184.1; 424/192.1; 530/300; 514/2

(58) Field of Classification Search ........................ None
See application file for complete search history.

(56) References Cited

U.S. PATENT DOCUMENTS

| | | | |
|---|---|---|---|
| 4,275,149 A | 6/1981 | Litman et al. |
| 4,318,980 A | 3/1982 | Boguslaski et al. |
| 4,676,980 A | 6/1987 | Segal et al. |
| 5,192,679 A | 3/1993 | Dawson et al. |
| 5,401,656 A | 3/1995 | Dawson |
| 5,413,931 A | 5/1995 | Dawson et al. |
| 5,726,010 A | 3/1998 | Clark |
| 5,789,176 A | 8/1998 | Dawson et al. |
| 5,869,335 A | 2/1999 | Munderloh et al. |
| 5,928,879 A | 7/1999 | Dumler et al. |
| 5,955,359 A | 9/1999 | Dumler et al. |
| 5,976,791 A | 11/1999 | Mabilat et al. |
| 5,976,860 A | 11/1999 | Coughlin et al. |
| 5,989,848 A | 11/1999 | Dawson |
| 6,015,691 A | 1/2000 | Walker et al. |
| 6,025,338 A | 2/2000 | Barbet et al. |
| 6,034,085 A | 3/2000 | Joshi et al. |
| 6,204,252 B1 | 3/2001 | Murphy et al. |
| 6,207,169 B1 | 3/2001 | Reed et al. |
| 6,231,869 B1 | 5/2001 | Reed et al. |
| 6,251,872 B1 | 6/2001 | Barbet et al. |
| 6,277,381 B1 | 8/2001 | Reed et al. |
| 6,284,238 B1 | 9/2001 | Coughlin et al. |
| 6,306,394 B1 | 10/2001 | Murphy et al. |
| 6,306,402 B1 | 10/2001 | Reed et al. |
| 6,355,777 B1 | 3/2002 | Walker et al. |
| 6,392,023 B1 | 5/2002 | Walker et al. |
| 6,403,780 B1 | 6/2002 | Walker et al. |
| 6,458,942 B1 | 10/2002 | Walker et al. |
| 6,593,147 B1 | 7/2003 | Barbet et al. |
| 7,087,372 B2 | 8/2006 | Lawton et al. |
| 2002/0064531 A1 | 5/2002 | Wlker et al. |
| 2002/0064535 A1 | 5/2002 | Reed et al. |
| 2002/0068343 A1 | 6/2002 | Reed et al. |
| 2002/0086984 A1 | 7/2002 | Reed et al. |
| 2002/0115840 A1 | 8/2002 | Walker et al. |
| 2002/0120115 A1 | 8/2002 | Rikihisa et al. |
| 2002/0132789 A1 | 9/2002 | Barbet et al. |
| 2002/0160432 A1 | 10/2002 | Lawton et al. |
| 2002/0177178 A1 | 11/2002 | Lawton et al. |
| 2003/0119082 A1 | 6/2003 | Lawton et al. |
| 2003/0129680 A1 | 7/2003 | O'Connor |
| 2003/0194756 A1 | 10/2003 | O'Connor |
| 2003/0194757 A1 | 10/2003 | O'Connor et al. |
| 2005/0124015 A1 | 6/2005 | O'Connor et al. |
| 2006/0189537 A1 | 8/2006 | O'Connor |
| 2006/0211062 A1 | 9/2006 | O'Connor |
| 2007/0026474 A1 | 2/2007 | Lawton et al. |

FOREIGN PATENT DOCUMENTS

| | | | |
|---|---|---|---|
| WO | WO 99/13720 | * | 3/1999 |
| WO | WO 00/65064 | | 11/2000 |
| WO | WO 01/85949 | | 11/2001 |
| WO | 02/01395 | | 1/2002 |

(Continued)

OTHER PUBLICATIONS

Greenspan et al. (Nature Biotechnology 7: 936-937, 1999).*

(Continued)

*Primary Examiner*—N. M. Minnifield
*Assistant Examiner*—Vanessa L. Ford
(74) *Attorney, Agent, or Firm*—McDonnell Boehnen Hulbert & Berghoff LLP

(57) ABSTRACT

The invention provides methods and compositions for the detection of *Ehrlichia canis* and *Ehrlichia chaffeensis* antibodies and antibody fragments.

17 Claims, No Drawings

FOREIGN PATENT DOCUMENTS

| WO | WO 02/057794 A2 | 7/2002 |
| WO | 03/010131 | 4/2003 |
| WO | WO 06/138509 A2 | 12/2006 |

OTHER PUBLICATIONS

Bowie et al (Science, 1990, 257:1306-1310).*
McGuinnes et al. (Mol. Microbiol. 7: 505-514, Feb. 1993).*
McGuinnes et al. (Lancet 337: 514-517, Mar. 1991).*
Tam et al (Journal of Immunological Methods, 196 (1996), 17-32).*
Board of Patent Appeals and Interferences, Appeal No. 2005-1593, U.S. Appl. No. 10/054,647, Dec. 23, 2005.*
Board of Patent Appeals and Interferences, Appeal No. 2005-1610, U.S. Appl. No. 10/054,354, Dec. 22, 2005.*
Ohashi, et al., "Immunodominant Major Outer Membrane Proteins of *Ehrlichia chaffeensis* are Encoded by a Polymorphic Multigene Family", *Infection and Immunity*, 66, p. 132-139 (1998).
Ohashi, et al., "Cloning and Characterization of Multigenes Encoding the Immunodominant 30-Kilodalton Major Outer Membrane Proteins of *Ehrlichia canis* and Application of the Recombinant Protein for Serodiagnosis", *Journal of Clinical Microbiology*, 36, p. 2371-2680 (1998).
Yu, et al., "Genetic Diversity of the 28-Kilodalton Outer Membrane Protein Gene in Human Isolates of *Ehrlichia chaffeensis*", *Journal of Clinical Microbiology*, 37, p. 1137-1143 (1999).
McBride, et al., "Molecular Cloning of the Gene for a Conserved Major Immunoreactive 28-Kilodalton Protein of *Ehrlichia canis*: a Potential Serodiagnostic Antigen", *Clinical and Diagnostic Laboratory Immunology*, 6, p. 392-399 (1999).
Yu, et al., "Comparison of *Ehrlichia chaffeensis* Recombinant Proteins for Serologic Diagnosis of Human Monocytotropic Ehrlichiosis", *Journal of Clinical Microbiology*, 37, p. 2568-2575 (1999).
Yu, et al., "Characterization of the Complete Transcriptionally Active *Ehrlichia chaffeensis* 28 kDa Outer Membrane Protein Multigene Family", *Gene*, 248, p. 59-68 (2000).
McBride, et al., "A Conserved, Transcriptionally Action p28 Multigene Locus of *Ehrlichia canis*", *Gene* 254, p. 245-252 (2000).
Suksawat, et al., "Seroprevalence of *Ehrlichia canis*, *Ehrlichia equi*, and *Ehrlichia risticii*, in Sick Dogs from North Carolina and Virginia", *Journal of Vet. Internal. Med.*, 14, p. 50-55 (2000).
Waner, et al., "Comparison of a clinic-based ELISA test kit with the immunofluorescence test for the assay of *Ehrlichia canis* antibodies in dogs", *J. Vet. Diagn. Invest.*, 12:240-244 (2000).
Cadman, et al., "Comparison of the dot-blot enzyme linked immunoassay with immunofluorescence for detecting antibodies to *Ehrlichia canis*", *Veterinary Record*, 135, 362 (1994).
Zhi, et al., "Cloning and expression of the 44-kilodalton major outer membrane protein gene of the human granulocytic ehrlichiosis agent and application of the recombinant protein to serodiagnosis", *Journal of Clinical Microbiology*, p. 1666-1673 (1998).
Unver, et al., "Western and dot blotting analyses of *Ehrlichia chaffeensis* indirect fluorescent-antibody assay-positive and -negative sera by using native and recombinant *E. chaffeensis* and *E. canis* antigens", *Journal of Clinical Microbiology*, p. 3888-3895 (1999).
McBride, et al., "Immunodiagnosis of *Ehrlichia canis* infection with recombinant proteins", *Journal of Clinical Microbiology*, 39:315-322 (2001).
Reddy, et al., "Molecular Characterization of a 28 kDa Surface Antigen Gene Family of the Tribe Ehrlichiae", *Biochemical and Biophysical Research Communications*, 247, p. 636-643 (1998).
O'Connor et al., "Comparison of an indirect immunofluorescence assay, western blot analysis, and a commercially available ELISA for detection of *Ehrlichia canis* antibodies in canine sera", *AJVR*. vol. 67, No. 2, p. 206-210 (2006).
U.S. Appl. No. 60/335,367, filed Oct. 31, 2001.
O'Connor, "Dogs Vaccinated with Common Lyme Disease Vaccines do not Respond to IR6, the Conserved Immunodominant Region of the VIsE Surface Protein of Borrelia burgdorferi", Clinical and Diagnostic Laboratory Immunology, May 2004, p. 458-462 (2004).
Harrus, et al., "Comparison of three enzyme-linked immunosorbant assays with the indirect immunofluorescent antibody test for the diagnosis of canine infection with *Ehrlichia canis*", Veterinary Microbiology, 86 (2002) 361-368.
Köhler, et al., "Continuous cultures of Fused Cells Secreting Antibody of Predefined Specificity", Nature, vol. 256, pp. 495-497, 1975.
Bowie, et al., "Deciphering the Message in Protein Sequences: Tolerance to Amino Acid Substitutions", Science, vol. 247, pp. 1306-1310, 1990.
Cunningham, et al., "High-Resolution Eptiope Mapping of hGH-Receptor Interactions by Alanine-Screening Mutagenesis", Science, vol. 244, p. 1081-1085, 1989.
Wright, et al., "Genetically Engineered Antibodies: Progress and Prospects", Critical Reviews in Immunology, 12(3,4):125-168, 1992.
Morrison, "In Vitro Antibodies: Strategies for Production and Application", Annu. Rev. Immunol., 10:239-65, 1992.
Dean, "Preparation and Testing of Monoclonal Antibodies to Recombinant Proteins", Methods in Molecular Biology, vol. 80, p. 23-37, 1994.
Dean, Preparation and characterization of Monoclonal Antibodies to Proteins and Other Cellular Components:, Methods in Molecular Biology, vol. 32, pp. 361-379, 1994.
Bailey, "The Raising of a Polyclonal Antiserum to a Protein", Methods in Molecular Biology, vol. 32, pp. 381-388, 1994.
Gullick, "Production of Antisera to Synthetic Peptides", Methods in Molecular Biology, vol. 32, pp. 389-399, 1994.
Tam, "Recent advances in multiple antigen peptides", Journal of Immunological Methods 196 (1996) 17-32.
Greenspan, et al., "Defining epitopes: It's not as easy as it seems", Nature Biotechnology, vol. 17, pp. 936-937 (1999).
McGuinness, et al., "Point mutation in menigococcal por A gene associates with increased endemic disease", The Lancet, vol. 337, pp. 514-517 (1991).
McGuinness, et al., "Class 1 outer membrane protein of Neisseria meningitidis: epitope analysis of the antigenic diversity between strains, implications for subtype definition and moleuclar epidemiology", Molecular Microbiology, (1993) 7(4), 505-514.

* cited by examiner

COMPOSITIONS AND METHODS FOR DETECTION OF *EHRLICHIA CANIS* AND *EHRLICHIA CHAFFEENSIS* ANTIBODIES

PRIORITY

This application is a continuation of U.S. application Ser. No. 10/054,647, filed Jan. 22, 2002, abandoned, which is a divisional of U.S. application Ser. No. 09/765,739, filed Jan. 18, 2001, now U.S. Pat. No. 7,087,372, which are incorporated herein by reference in their entirety. This application is also a continuation of PCT/US02/01395, filed Jan. 16, 2002.

TECHNICAL AREA OF THE INVENTION

The invention provides compositions and methods for the detection and quantification of *Ehrlichia canis* and *Ehrlichia chaffeensis* antibodies and antibody fragments.

BACKGROUND OF THE INVENTION

The *Ehrlichia* are obligate intracellular pathogens that infect circulating lymphocytes in mammalian hosts. *Ehrlichia canis* and *Ehrlichia chaffeensis* are members of the same sub-genus group that infect canines and humans and cause canine monocytic ehrlichiosis (CME) and human monocytic ehrlichiosis (HME), respectively. The canine disease is characterized by fever, lymphadenopathy, weight loss, and pancytopenia. In humans the disease is characterized by fever, headache, mylagia, and leukopenia. Early detection and treatment are important for treating both canine and human ehrlichiosis.

Indirect immunofluorescense assays (IFA) and enzyme-linked immunosorbent assays (ELISA) are frequently used as aids in the diagnosis of these diseases. These assays measure or otherwise detect the binding of anti-*Ehrlichia* antibodies from a patient's blood, plasma, or serum to infected cells, cell lysates, or purified *Ehrlichia* proteins. However, currently known assays for detecting anti-*Ehrlichia* antibodies or fragments thereof are severely limited in usefulness because of sensitivity and specificity issues directly related to the impure nature of the *Ehrlichia* antigen used in these tests. Highly purified reagents are needed to construct more accurate assays.

SUMMARY OF THE INVENTION

It is an object of the invention to provide reagents and methods for detecting anti-*Ehrlichia canis* antibodies and anti-*Ehrlichia chaffeensis* antibodies. This and other objects of the invention are provided by one or more of the embodiments described below.

One embodiment of the invention provides a composition of matter comprising an isolated polypeptide selected from the group consisting of SEQ ID NO: 1, SEQ ID NO:2, SEQ ID NO:3, SEQ ID NO:4, SEQ ID NO:5, SEQ ID NO:6, SEQ ID NO:7, and variants thereof.

Another embodiment of the invention provides a composition of matter comprising an isolated polypeptide selected from the group consisting of SEQ ID NO: 1, SEQ ID NO:2, SEQ ID NO:3, SEQ ID NO:4, SEQ ID NO:5, SEQ ID NO:6, SEQ ID NO:7, and variants thereof, and a carrier.

Still another embodiment of the invention provides a method of detecting the presence of antibodies to *Ehrlichia*. The method comprises contacting one or more polypeptides selected from the group consisting of the polypeptides shown in SEQ ID NO:1, SEQ ID NO:2, SEQ ID NO:3, SEQ ID NO:4, SEQ ID NO:5, SEQ ID NO:6, SEQ ID NO:7, and variants thereof, with a test sample suspected of comprising antibodies to *Ehrlichia*, under conditions that allow polypeptide/antibody complexes to form. The polypeptide/antibody complexes are detected. The detection of polypeptide/antibody complexes is an indication that antibodies to *Ehrlichia* are present in the test sample.

Yet another embodiment of the invention provides a device containing one or more polypeptides selected from the group consisting of the polypeptides shown in SEQ ID NO:1, SEQ ID NO:2, SEQ ID NO:3, SEQ ID NO:4, SEQ ID NO:5, SEQ ID NO:6, SEQ ID NO:7, and variants thereof, and instructions for use of the one or more polypeptides for the identification of an *Ehrlichia* infection in a mammal.

Still another embodiment of the invention provides an article of manufacture comprising packaging material and, contained within the packaging material, one or more polypeptides selected from the group consisting of the polypeptides shown in SEQ ID NO:1, SEQ ID NO:2, SEQ ID NO:3, SEQ ID NO:4, SEQ ID NO:5, SEQ ID NO:6, SEQ ID NO:7, and variants thereof. The packaging material comprises a label that indicates that the one or more polypeptides can be used for the identification of *Ehrlichia* infection in a mammal.

Even another embodiment of the invention provides a method of diagnosing an *Ehrlichia* infection in a mammal. The method comprises obtaining a biological sample from a mammal suspected of having an *Ehrlichia* infection, and contacting one or more polypeptides selected from the group consisting of the polypeptides shown in SEQ ID NO:1, SEQ ID NO:2, SEQ ID NO:3, SEQ ID NO:4, SEQ ID NO:5, SEQ ID NO:6, SEQ ID NO:7, and variants thereof, with the biological sample under conditions that allow polypeptide/antibody complexes to form. Polypeptide/antibody complexes are detected, wherein the detection of polypeptide/antibody complexes is an indication that the mammal has an *Ehrlichia* infection.

Another embodiment of the invention provides a monoclonal antibody that specifically binds to at least one epitope of an *Ehrlichia canis* or *Ehrlichia chaffeensis* polypeptide selected from the group consisting of SEQ ID NO: 1, SEQ ID NO:2, SEQ ID NO:3, SEQ ID NO:4, SEQ ID NO:5, SEQ ID NO:6, and SEQ ID NO:7.

The invention therefore provides highly purified polypeptides and antibodies for use in accurate assays for the detection of *Ehrlichia* antibodies and antibody fragments.

DETAILED DESCRIPTION OF THE INVENTION

Polypeptides of the Invention

The invention provides highly purified reagents for the detection of *E. canis* and *E. chaffeensis* antibodies and antibody fragments. In particular, the invention provides polypeptides having at least 85% identity, more preferably at least 90% identity, and still more preferably at least 96%, 97%, 98%, or 99% identity to a polypeptide sequence shown in SEQ ID NOs:1-7. See Table 1. Polypeptides that do not comprise 100% identity to a polypeptide sequence shown in SEQ ID NOs:1-7 are considered "variants," and are considered polypeptides of the invention.

The *E. canis* peptides were identified using phage display technology by determining the amino acid sequence bound by a mouse monoclonal antibody (IIIH7) raised against native *E. canis* antigen. The IIIH7 monoclonal antibody was used to affinity purify virus-expressing peptides in a PDH 10 phage display library. The sequences or mimetopes bound by IIIH7 demonstrated strong sequence homology to outer membrane proteins of *E. canis* and *E. chaffeensis*. The outer membrane proteins of both species are encoded by a polymorphic gene family, which results in multiple reproductions of the proteins.

TABLE 1

| SEQ ID NO | Sequence of Peptide | Peptide Derived From |
|---|---|---|
| SEQ ID NO:1 | KSTVGVFGLKHDWDGSPILK | *E. canis* P30-1 |
| SEQ ID NO:2 | NTTTGVFGLKQDWDGATIKD | *E. canis* P30 |
| SEQ ID NO:3 | NTTVGVFGLKQNWDGSAISN | *E. chaffeesis* P28 |
| SEQ ID NO:4 | NPTVALYGLKQDWNGVSA | *E. chaffeesis* OMP-1C |
| SEQ ID NO:5 | NTTVGVFGIEQDWDRCVIS | *E. chaffeesis* OMP-1D |
| SEQ ID NO:6 | NPTVALYGLKQDWEGISS | *E. chaffeesis* OMP-1E |
| SEQ ID NO:7 | NTTTGVFGLKQDWDGSTIS | *E. chaffeesis* OMP-1F |

Identity means amino acid sequence similarity and has an art recognized meaning. Sequences with identity share identical or similar amino acids, where similar amino acids are preferably conserved amino acids. Conserved amino acids are amino acids that possess similar side chains and properties (e.g., hydrophilic, hydrophobic, aromatic) as the amino acids encoded by the reference sequence. Thus, a candidate sequence sharing 85% amino acid sequence identity with a reference sequence (i.e., SEQ ID NOs:1-7) requires that, following alignment of the candidate sequence with the reference sequence, 85% of the amino acids in the candidate sequence are identical to the corresponding amino acids in the reference sequence, and/or constitute conservative amino acid changes.

Sequences are aligned for identity calculations using a mathematical algorithm, such as the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the XBLAST programs of Altschul et al. (1990) *J. Mol. Biol.* 215:403-410. BLAST protein searches can be performed with the XBLAST program, score=50, wordlength=3 to obtain amino acid sequences with identity to the polypeptides of the invention. To obtain gapped alignments for comparison purposes, Gapped BLAST can be utilized as described in Altschul et al. (1997) *Nucleic Acids Res.* 25:3389-3402. When utilizing BLAST and Gapped BLAST programs, the default parameters of the respective programs (e.g., XBLAST) can be used. Internal gaps and amino acid insertions in the candidate sequence as aligned are ignored when making the identity calculation.

Variants in which amino acids of the polypeptides of the invention are substituted, deleted, or added in any combination are contemplated by the invention. Naturally occurring variants and non-naturally occurring variants are included in the invention and may be produced by mutagenesis techniques or by direct synthesis.

Using known methods of protein engineering and recombinant DNA technology, variants may be generated to improve or alter the characteristics of the polypeptides of the present invention. Such variants include deletions, insertions, inversions, repeats, and substitutions selected according to general rules known in the art so as have little effect on activity. For example, guidance concerning how to make phenotypically silent amino acid substitutions is provided in Bowie et al., *Science,* 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, the amino acid positions which have been conserved between species can be identified. These conserved amino acids are likely important for protein function. In contrast, the amino acid positions in which substitutions have been tolerated by natural selection indicate positions which are not critical for protein function. Thus, positions tolerating amino acid substitution may be modified while still maintaining specific binding activity of the polypeptide to anti-*Ehrlichia* antibodies or antibody fragments.

The second strategy uses genetic engineering to introduce amino acid changes at specific positions of a cloned gene to identify regions critical for protein function. For example, site-directed mutagenesis or alanine-scanning mutagenesis (the introduction of single alanine mutations at every residue in the molecule) can be used (Cunningham et al., *Science,* 244:1081-1085 (1989)). The resulting mutant molecules can then be tested for specific binding to anti-*Ehrlichia* antibodies or antibody fragments.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln; replacement of the basic residues Lys, Arg, and His; replacement of the aromatic residues Phe, Tyr, and Trp; and replacement of the small-sized amino acids Ala, Ser, Thr, Met, and Gly.

Besides conservative amino acid substitution, variants of the present invention include: (i) substitutions with one or more of the non-conserved amino acid residues, where the substituted amino acid residues may or may not be one encoded by the genetic code; (ii) substitution with one or more of amino acid residues having a substituent group; (iii) fusion of the mature polypeptide with another compound, such as a compound to increase the stability and/or solubility of the polypeptide (e.g., polyethylene glycol); (iv) fusion of the polypeptide with additional amino acids, such as an IgG Fc fusion region peptide, a leader or secretory sequence, or a sequence facilitating purification. Such variant polypeptides are deemed to be within the scope of those skilled in the art from the teachings herein.

Polypeptides of the invention specifically bind to an anti-*Ehrlichia* antibody. In this context "specifically binds" means that the polypeptide recognizes and binds to an anti-*Ehrlichia* antibody, but does not substantially recognize and bind other molecules in a test sample.

Polypeptides of the invention comprise at least one epitope that is recognized by an anti-*Ehrlichia* antibody. An epitope is an antigenic determinant of a polypeptide. An epitope can be a linear, sequential epitope or a conformational epitope. Epitopes within a polypeptide of the invention can be identified by several methods. See, e.g., U.S. Pat. No. 4,554,101; Jameson & Wolf, *CABIOS* 4:181-186 (1988). For example, a polypeptide of the invention can be isolated and screened. A series of short peptides, which together span the entire polypeptide sequence, can be prepared by proteolytic cleavage. By starting with, for example, 20-mer polypeptide fragments, each fragment can be tested for the presence of epitopes recognized in, for example, an enzyme-linked immunosorbent assay (ELISA). In an ELISA assay a polypeptide, such as a 20-mer polypeptide fragment, is attached to a solid support, such as the wells of a plastic multi-well plate. A population of antibodies are labeled, added to the solid support and allowed to bind to the unlabeled antigen, under conditions where non-specific adsorption is blocked, and any unbound antibody and other proteins are washed away. Antibody binding is detected by, for example, a reaction that converts a colorless indicator reagent into a colored reaction product. Progressively smaller and overlapping fragments can then be tested from an identified 20-mer to map the epitope of interest.

Preferably, a polypeptide of the invention is synthesized using conventional peptide sythesizers, which are well known in the art. A polypeptide of the invention can also be produced recombinantly. A polynucleotide encoding an *Ehrlichia* polypeptide can be introduced into an expression vector that can be expressed in a suitable expression system using techniques well known in the art. A variety of bacterial, yeast, plant, mammalian, and insect expression systems are available in the art and any such expression system can be used. Optionally, a polynucleotide encoding an *Ehrlichia* polypeptide can be translated in a cell-free translation system.

If desired, an *Ehrlichia* polypeptide can be produced as a fusion protein, which can also contain other amino acid sequences, such as amino acid linkers or signal sequences, as well as ligands useful in protein purification, such as glutathione-S-transferase, histidine tag, and staphylococcal protein A. More than one *Ehrlichia* polypeptide can be present in a fusion protein. If desired, various combinations of *Ehrlichia* polypeptides from different *ehrilichia* strains or isolates can be included in a fusion protein.

A polypeptide of the invention can be synthesized such that it comprises several repeated *Ehrlichia* polypeptides. This is a multimeric polypeptide. These repeated polypeptides can comprise one specific polypeptide, e.g. the polypeptide shown in SEQ ID NO: 1, repeated 2 or more times. Alternatively, the repeated polypeptides can comprise one or more copies of a specific *Ehrlichia* polypeptide along with one or more copies of another different *Ehrlichia* polypeptide. A polypeptide of the invention can be combined or synthesized with one or more polypeptides, fragments of polypeptides, or full-length polypeptides. Preferably the one or more polypeptides are other polypeptides of the invention or other *Ehrlichia* proteins.

Polypeptides of the invention can also comprise fragments of the polypeptides shown in SEQ ID NO: 1-7, or variants thereof. For example, fragments of polypeptides can comprise any number of amino acids between 6 and 20 amino acids.

A polypeptide of the invention is preferably combined with a carrier. A carrier is a vehicle for a polypeptide of the invention. Carriers include, for example, excipients, diluents, adjuvants, and stabilizers. Examples of such stabilizers are proteins such as serum albumins and gelatin; saccharides such as glucose, sucrose, lactose, maltose, trehalose, sorbitol, maltitol, mannitol and lactitol; and buffers which are mainly composed of phosphate or succinate.

Various strains and isolates of *Ehrlichia canis* and *Ehrlichia chaffeensis* occur, and polypeptides of any of these strains and isolates can be used in the present invention. Nucleic acid and amino acid sequences of *Ehrlichia* genes and polypeptides are known in the art. For example, several sequences of the *E. chaffeensis* OMP gene family and several sequences of the *E. canis* P30 gene family are disclosed in WO 99/13720.

Methods of Detection

The methods of the invention detect *Ehrlichia canis* or *Ehrlichia chaffeensis* antibodies or antibody fragments in a test sample, such as a biological sample, an environmental sample, or a laboratory sample. A biological sample can include, for example, sera, blood, cells, plasma, or tissue from a mammal such as a dog or a human. The test sample can be untreated, precipitated, fractionated, separated, diluted, concentrated, or purified before combining with a polypeptide of the invention.

The methods comprise contacting a polypeptide of the invention with a test sample under conditions that allow a polypeptide/antibody complex to form. The formation of a complex between the polypeptide and anti-*Ehrlichia* antibodies in the sample is detected. In one embodiment of the invention, the polypeptide/antibody complex is detected when an indicator reagent, such as an enzyme, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

Assays of the invention include, but are not limited to those based on competition, direct reaction or sandwich-type assays. Assays can use solid phases or substrates or can be performed by immunoprecipitation or any other methods which do not utilize solid phases. Where a solid phase or substrate is used, a polypeptide of the invention is directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). A preferred substrate is sintered, fine particles of polyethylene, commonly known as porous polyethylene, for example, 10-15 micron porous polyethylene from Chromex Corporation. All of these substrate materials may be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

Polypeptides of the invention can be used to detect anti-*Ehrlichia* antibodies or antibody fragments in assays including, but not limited to enzyme linked immunosorbent assay (ELISA), western blot, IFA, radioimmunoassay (RIA), hemagglutination (HA), and fluorescence polarization immunoassay (FPIA). A preferred assay of the invention is the reversible flow chromatographic binding assay, for example a SNAP® assay. See U.S. Pat. No. 5,726,010.

In one type of assay format, one or more polypeptides can be coated on a solid phase or substrate. A test sample suspected of containing anti-*Ehrlichia* antibodies is incubated with an indicator reagent comprising a signal generating compound conjugated to an antibody specific for *Ehrlichia* for a time and under conditions sufficient to form antigen/antibody complexes of either antibodies of the test sample to the polypeptides of the solid phase or the indicator reagent compound conjugated to an antibody specific for *Ehrlichia* to the polypeptides of the solid phase. The reduction in binding of the indicator reagent conjugated to an anti-*Ehrlichia* antibody to the solid phase can be quantitatively measured. A measurable reduction in the signal compared to the signal generated from a confirmed negative *Ehrlichia* test sample indicates the presence of anti-*Ehrlichia* antibody in the test sample. This type of assay can quantitate the amount of anti-*Ehrlichia* antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If *Ehrlichia* antibodies are present in the test sample they will bind the polypeptide conjugated to an indicator reagent and to the polypeptide immobilized on the support. The polypeptide/antibody/indicator complex can then be detected. This type of assay can quantitate the amount of anti-*Ehrlichia* antibodies in a test sample.

The formation of a polypeptide/antibody complex or a polypeptide/antibody/indicator complex can be detected by radiometric, colormetric, fluorometric, size-separation, or precipitation methods. Optionally, detection of the polypeptide/antibody complex is by the addition of a secondary antibody that is coupled to a indicator reagent comprising a signal generating compound. Indicator reagents comprising signal generating compounds (labels) associated with a polypeptide/antibody complex can be detected and include chromogenic agents, catalysts such as enzymes, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzymes include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-*E. canis* or anti-*E. chaffeensis* antibodies in a test sample. Therefore, the methods of the invention can be used to diagnose *E. canis* or *E. chaffeensis* infection in a patient. Each polypeptide of the invention can detect *E. canis* or *E. chaffeensis* or both due to cross-reactivity of the polypeptides and antibodies.

The methods of the invention can also indicate the amount or quantity of anti-*Ehrlichia* antibodies in a test sample. With many indicator reagents, such as enzymes, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples which previously have been diluted, or concentrate specimens such as urine, in order to determine the presence and/or amount of antibody present.

The invention further comprises assay kits for detecting anti-*Ehrlichia* antibodies in a sample. A kit comprises one or more polypeptides of the invention and means for determining binding of the polypeptide to *Ehrlichia* antibodies in the sample. A kit can comprise a device containing one or more polypeptides of the invention and instructions for use of the one or more polypeptides for the identification of an *Ehrlichia* infection in a mammal. The kit can also comprise packaging material comprising a label that indicates that the one or more polypeptides of the kit can be used for the identification of *Ehrlichia* infection. Other components such as buffers, controls, and the like, known to those of ordinary skill in art, may be included in such test kits. The polypeptides, assays, and kits of the invention are useful, for example, in the diagnosis of individual cases of *Ehrlichia* infection in a patient, as well as epidemiological studies of *Ehrlichia* outbreaks.

Polypeptides and assays of the invention can be combined with other polypeptides or assays to detect the presence of *Ehrlichia* along with other organisms. For example, polypeptides and assays of the invention can be combined with reagents that detect heartworm and/or *Borrelia burgdorferi*.

Monoclonal Antibodies

The polypeptides of the invention can also be used to develop monoclonal and/or polyclonal antibodies that specifically bind to an immunological epitope of *E. canis* or *E. chaffeensis* present in the polypeptides of the invention.

The antibodies or fragments thereof can be employed in assay systems, such as a reversible flow chromatographic binding assay, enzyme linked immunosorbent assay, western blot assay, or indirect immunofluorescense assay, to determine the presence, if any, of *Ehrlichia* polypeptides in a test sample. In addition, these antibodies, in particular monoclonal antibodies, can be bound to matrices similar to CNBr-activated Sepharose and used for the affinity purification of specific *Ehrlichia* proteins from, for example, cell cultures or blood serum, such as to purify recombinant and native *Ehrlichia* antigens and proteins. The monoclonal antibodies of the invention can also be used for the generation of chimeric antibodies for therapeutic use, or other similar applications.

Monoclonal antibodies directed against *Ehrlichia* epitopes can be produced by one skilled in the art. The general methodology for producing such antibodies is well-known and has been described in, for example, Kohler and Milstein, Nature 256:494 (1975) and reviewed in J. G. R. Hurrel, ed., Monoclonal Hybridoma Antibodies: Techniques and Applications, CRC Press Inc., Boca Raton, Fla. (1982), as well as that taught by L. T. Minims et al., *Virology* 176:604-619 (1990). Immortal antibody-producing cell lines can be created by cell fusion, and also by other techniques such as direct transformation of B lymphocytes with oncogenic DNA, or transfection with Epstein-Barr virus. The following are provided for exemplification purposes only and are not intended to limit the scope of the invention described in broad terms above. All references cited in this disclosure are incorporated herein by reference.

EXAMPLES

Example 1

Detection of *E. Canis* Antibodies in Canine Serum

The performance of a reversible flow chromatographic binding assay, a synthetic peptide SNAP® assay was compared to the performance of a commercially available reversible flows chromatographic *E. canis* SNAP® assay that uses partially purified *E. canis* antigens. The partially purified native antigens were obtained from *E. canis* organisms grown in tissue culture and partially purified by differential centrifugation and column chromatography. The synthetic peptides used in the reversible flow chromatographic synthetic peptide SNAP® assay were monomeric forms of the *E. canis* P30-1 or the *E. canis* P-30 peptide, SEQ ID NO: 1 and SEQ ID NO:2, respectively.

A population of 70 suspected *E. canis* positive canine samples was obtained from Arizona, Texas, and Arkansas and tested using the reversible flow chromatographic synthetic peptide SNAP® assay and the reversible flow chromatographic native antigen SNAP® assay. The samples were also tested using an indirect IFA. Briefly, the IFA assay was performed using *E. canis* infected cells coated onto IFA slides and fluorescein isothiocyanate (FITC)-labeled rabbit anti-canine IgG. *E. canis* was harvested from cell cultures, diluted in buffer and coated onto IFA slides. Dilutions of test samples were made in buffer, incubated with the coated IFA slides, and then washed and incubated with FITC-labeled anti-canine conjugate. Slides were washed and viewed by with ultraviolet light microscopy. IFA results are recorded as a titer of fluorescence activity. This represents the last sample dilution reactive on the IFA slide. Samples with IFA titers greater than or equal to 1:100 are positive.

In the case of discrepant results, an *E. canis* western blot was used as the confirmatory assay. Briefly, *E. canis* antigen was harvested from tissue culture, resolved by SDS-polyacrylamide gel electrophoresis (SDS-PAGE) and then transferred to a nitrocellulose membrane. After transfer, the membrane was blocked with heterologous protein overnight at 4 degrees C. Diluted test samples of canine *E. canis* Ab-positive and negative serum samples were incubated with blots for 2 hours at room temperature. Blots were then washed, incubated with commercial anti-canine IgG:peroxidase conjugate reagents for 1 hour and washed. Signals were developed by incubation of strips with a commercial peroxidase indicator reagent. Reaction to the immunodominat band with a molecular weight of 30,000 Daltons was required for positive result confirmation by western blot. See, e.g., Suksawat et al. *J. Vet. Internal Med.* 14:50-55 (2000).

The reversible flow chromatographic synthetic peptide SNAP® assay and reversible flow chromatographic native antigen SNAPS® assay comprised an assay system similar to that described in U.S. Pat. No. 5,726,010. Briefly, a test sample is applied to a reverse flow chromatographic binding assay device and allowed to flow along and saturate a flow matrix. This facilitates sequential complex formation. That is, an *Ehrlichia* antibody in the test sample binds first to an non-immobilized labeled specific binding reagent. In the case of the reversible flow chromatographic synthetic peptide SNAPS® assay the non-immobilized labeled specific binding reagent is a polypeptide of the invention conjugated to horseradish peroxidase. For the reversible flow chromatographic native antigen SNAP® assay the reagent comprises partially purified native antigens. This complex binds to an immobilized analyte capture reagent. For the reversible flow chromatographic synthetic peptide SNAP® assay the immobilized analyte capture reagent is one or more polypeptides of the invention conjugated to bovine serum albumin. For the reversible flow chromatographic native antigen SNAP® assay the capture reagent is partially purified native antigens. An absorbent reservoir is contacted with the saturated flow matrix, thereby reversing the fluid flow. Detector and wash solution is delivered to the flow matrix. The liquid reagents remove unbound sample and unbound labeled specific binding reagent and facilitate detection of analyte complexes at the location of the of the immobilized analyte capture reagent. The substrate used in these experiments was 3,3',5,5' tetramethylbenzidine (TMB).

Results

The results of the assays are shown in Table 2 (a comparison of reversible flow chromatographic native antigen SNAP® assay with reversible flow chromatographic synthetic peptide SNAP® assay). The results can be broken into five groups.

Group 1 comprises forty-seven samples that were positive according to the reversible flow chromatographic synthetic peptide SNAP® assay, the reversible flow chromatographic native antigen SNAP® assay, and the IFA. These are antibody positive samples and no additional testing was done on these samples.

Group 2 comprises ten samples (numbers 15, 17, 18, 20, 22, 23, 24, 41, 42, and 46) that were positive according to the synthetic peptide SNAP® assay, negative according to the reversible flow chromatographic native antigen SNAP® assay, positive on the IFA, and confirmed by western blot analysis. These are true positive samples that were positive on the reversible flow chromatographic synthetic peptide SNAP® assay and false negative on the reversible flow chromatographic native antigen SNAP® assay.

Group 3 comprises five samples (numbers 1, 2, 3, 4, and 5) that were positive according to IFA and confirmed negative by western blot analysis. These are true negative samples that were false positive in the IFA. All 5 of these samples were correctly identified as negative by the reversible flow chromatographic synthetic peptide SNAP® assay. The reversible flow chromatographic native antigen SNAP® assay correctly identified three of the samples (numbers 1, 2, and 5) as negative, but gave false positive results for two samples (numbers 3 and 4).

Group 4 comprises seven samples (6, 7, 8, 9, 10, 11, and 12) that were negative by IFA and confirmed positive by western blot analysis. These are positive samples that were false negatives in the IFA. All seven samples were true positive on the reversible flow chromatographic synthetic peptide SNAP® assay. The reversible flow chromatographic native antigen SNAP® assay correctly identified only two of the seven samples (numbers 7 and 11) as positive and incorrectly identified five of the samples (numbers 6, 8, 9, 10, and 12) resulting in false negative results for these five samples.

Group 5 comprises one sample (number 21) that was positive by IFA and confirmed as positive by western blot analysis. The reversible flow chromatographic synthetic peptide SNAP® assay and the reversible flow chromatographic native antigen SNAP® assay gave negative results. This is a positive sample that was false negative on both the reversible flow chromatographic synthetic peptide SNAPS® assay and the reversible flow chromatographic native antigen SNAP® assay.

Therefore, 70 samples were tested and 65 of these samples were true positive samples. The reversible flow chromatographic synthetic peptide SNAPS® assay correctly identified 64 of the positive samples for a sensitivity of 98.5% (64/65). The reversible flow chromatographic native antigen SNAP® assay correctly identified 49 of the samples for a sensitivity of 75.3% (49/65). Of the five true negative samples, the reversible flow chromatographic synthetic peptide SNAP® assay correctly identified 5 of the negative samples for a specificity of 100% (5/5). The reversible flow chromatographic native antigen SNAPS® assay correctly identified 3 of the negative samples for a specificity of 60% (3/5). Therefore, the reversible flow chromatographic synthetic peptide SNAPS® assay is more sensitive and specific than the reversible flow chromatographic native antigen SNAP® assay.

TABLE 2

E. canis Ab Positive Canine Population Comparison of Native Antigen SNAP Assay with Synthetic Peptide SNAP Assay

| No. | Sample I.D. | Native Ag Assay 291JS | | Synthetic Peptide Assay 358HT & 359HT | | E. Canis IFA Titer≧ | Western Blot |
|---|---|---|---|---|---|---|---|
| | | E. Canis | H. Worm | E. Canis | H. Worm | | |
| 1 | F119894-6 | − | − | − | − | 1:100 | − |
| 2 | F103638-5 | − | − | − | − | 1:100 | − |
| 3 | 2815:89E | + | − | − | − | 1:100 | − |
| 4 | 31365 | + | − | − | − | 1:100 | − |
| 5 | F107158-1 | − | − | − | − | 1:400 | − |
| 6 | 31285 | − | − | + | − | − | + |
| 7 | 31508 | + | − | + | − | − | + |
| 8 | 31364 | − | − | + | − | − | + |
| 9 | 31037 | − | − | + | − | − | + |
| 10 | 31492 | − | − | + | − | − | + |
| 11 | 28963 | + | − | + | − | − | + |
| 12 | 31398 | − | − | + | − | − | + |
| 13 | 31527 | + | − | + | − | 1:100 | + |
| 14 | 31552 | + | − | + | − | 1:100 | + |
| 15 | 31556 | + | − | + | − | 1:100 | + |
| 16 | F101938-4 | + | − | + | − | 1:100 | + |
| 17 | 28404 | − | − | + | − | 1:100 | + |
| 18 | F102890-0 | − | − | + | − | 1:100 | + |
| 19 | 31496 | + | − | + | − | 1:100 | not done |
| 20 | 29825 | − | − | + | − | 1:400 | + |
| 21 | F099609-2 | − | − | − | − | 1:400 | + |
| 22 | F121120-6 | − | − | + | − | 1:400 | + |
| 23 | F104088-9 | − | − | + | − | 1:400 | + |
| 24 | F120923-5 | − | − | + | − | 1:400 | + |
| 25 | 31368 | + | − | + | − | 1:400 | not done |
| 26 | 31159 | + | − | + | − | 1:400 | not done |
| 27 | 2815:89A | + | − | + | − | 1:500 | not done |
| 28 | 2815:89B | + | + | + | + | 1:500 | not done |
| 29 | 2815:89C | + | − | + | − | 1:500 | not done |
| 30 | 2815:89D | + | − | + | − | 1:500 | not done |
| 31 | 30597 | + | − | + | − | 1:1600 | not done |
| 32 | 30448 | + | − | + | − | 1:1600 | not done |
| 33 | 29938 | + | − | + | − | 1:1600 | not done |
| 34 | 31500 | + | − | + | − | 1:1600 | not done |
| 35 | 31249 | + | − | + | − | 1:1600 | not done |
| 36 | 31369 | + | − | + | − | 1:1600 | not done |
| 37 | 31523 | + | − | + | − | 1:1600 | not done |
| 38 | 31021 | + | − | + | − | 1:1600 | not done |
| 39 | 30846 | + | − | + | − | 1:1600 | not done |
| 40 | 31536 | + | − | + | − | 1:1600 | not done |
| 41 | F102996-1 | − | − | + | − | 1:1600 | + |
| 42 | F118620-1 | − | − | + | − | 1:1600 | + |
| 43 | F104581-1 | + | − | + | − | 1:1600 | not done |
| 44 | P127 | + | + | + | + | 1:1600 | not done |
| 45 | 29363 | + | − | + | − | 1:1600 | not done |
| 46 | F120001-5 | − | − | + | − | 1:3200 | + |
| 47 | F107100-7 | + | − | + | − | 1:3200 | not done |
| 48 | F119153-3 | + | − | + | − | 1:3200 | not done |
| 49 | F120513-8 | + | − | + | − | 1:3200 | not done |
| 50 | F118601-4 | + | − | + | − | 1:3200 | not done |
| 51 | F121073-7 | + | − | + | − | 1:3200 | not done |
| 52 | 2898:62 | + | − | + | − | 1:3200 | not done |
| 53 | 28392 | + | − | + | − | 1:3200 | not done |
| 54 | 29375 | + | − | + | − | 1:3200 | not done |
| 55 | 29099 | + | − | + | − | 1:3200 | not done |
| 56 | 28580 | + | − | + | − | 1:3200 | not done |
| 57 | 28960 | + | − | + | − | 1:3200 | not done |
| 58 | 29361 | + | − | + | − | 1:3200 | not done |
| 59 | 30864 | + | − | + | − | 1:6400 | not done |
| 60 | 31158 | + | − | + | − | 1:6400 | not done |
| 61 | 31169 | + | − | + | − | 1:6400 | not done |
| 62 | 28094 | + | − | + | − | 1:6400 | not done |
| 63 | 28098 | + | − | + | − | 1:6400 | not done |
| 64 | 28174 | + | − | + | − | 1:6400 | not done |
| 65 | 28513 | + | − | + | − | 1:6400 | not done |
| 66 | 28830 | + | − | + | − | 1:6400 | not done |
| 67 | 28846 | + | − | + | − | 1:6400 | not done |
| 68 | 28914 | + | − | + | − | 1:6400 | not done |

TABLE 2-continued

*E. canis* Ab Positive Canine Population
Comparison of Native Antigen SNAP Assay with
Synthetic Peptide SNAP Assay

| No. | Sample I.D. | Native Ag Assay 291JS | | Synthetic Peptide Assay 358HT & 359HT | | *E. Canis* IFA Titer≧ | Western Blot |
|---|---|---|---|---|---|---|---|
| | | *E. Canis* | H. Worm | *E. Canis* | H. Worm | | |
| 69 | 17101 | + | − | + | − | 1:6400 | not done |
| 70 | 21120 | + | − | + | − | 1:6400 | not done |

We claim:

1. An isolated polypeptide consisting of the amino acid sequence of SEQ ID NO:2 or consisting of phenotypically silent amino acid substitution variants of the amino acid sequence of SEQ ID NO:2 that specifically bind to an anti-*Ehrlichia* antibody.

2. The isolated polypeptide of claim 1, further comprising a carrier.

3. The isolated polypeptide of claim 1, wherein the isolated polypeptide further comprises an indicator reagent.

4. A fusion protein comprising a first polypeptide consisting of the amino acid sequence of SEQ ID NO:2 or consisting of a phenotypically silent amino acid substitution variant of the amino acid sequence of SEQ ID NO:2, wherein the first polypeptide specifically binds to an anti-*Ehrlichia* antibody, and a second polypeptide comprising a heterologous polypeptide.

5. The fusion protein of claim 4, wherein the heterologous polypeptide is an *Ehrlichia* polypeptide, and wherein the heterologous polypeptide is not an *Ehrlichia canis* P30 polypeptide.

6. A multimeric polypeptide comprising two or more copies of the amino acid sequence of SEQ ID NO:2 or phenotypically silent amino acid substitution variants of the amino acid sequence of SEQ ID NO:2, wherein the amino acid substitution variants specifically bind to an anti-*Ehrlichia* antibody.

7. An isolated polypeptide consisting of the amino acid sequence of SEQ ID NO:2 or an isolated variant consisting of the polypeptide having at least 90% identity to the amino acid sequence of SEQ ID NO:2, wherein the isolated polypeptide specifically binds to an anti-*Ehrlichia* antibody.

8. The isolated polypeptide of claim 7, further comprising a carrier.

9. A fusion protein comprising a first polypeptide consisting of the amino acid sequence of SEQ ID NO:2 or an isolated variant consisting of the polypeptide having at least 90% identity to the amino acid sequence of SEQ ID NO:2, wherein the first polypeptide specifically binds to an anti-*Ehrlichia* antibody, and a second polypeptide comprising a heterologous polypeptide.

10. The fusion protein of claim 9, wherein the heterologous polypeptide is an *Ehrlichia* polypeptide, and wherein the heterologous polypeptide is not an *Ehrlichia canis* P30 polypeptide.

11. A multimeric polypeptide comprising two or more copies of the amino acid sequence of SEQ ID NO:2 or variants of the amino acid sequence of SEQ ID NO:2 having at least 90% identity to the amino acid sequence of SEQ ID NO:2, wherein the variants specifically bind to an anti-*Ehrlichia* antibody.

12. An isolated polypeptide consisting of the sequence of SEQ ID NO:2.

13. The isolated polypeptide of claim 12, wherein the polypeptide further comprises an indicator reagent.

14. The isolated polypeptide of claim 7, wherein the isolated variant consists of the polypeptide having at least 96% identity to the amino acid sequence of SEQ ID NO:2.

15. The isolated polypeptide of claim 7, wherein the isolated variant is an amino acid substitution variant of the amino acid sequence of SEQ ID NO:2.

16. The fusion protein of claim 9, wherein the isolated variant consists of the polypeptide having at least 96% identity to the amino acid sequence of SEQ ID NO:2.

17. The multimeric polypeptide of claim 11, wherein the variants of the amino acid sequence of SEQ ID NO:2 have at least 96% identity to the amino acid sequence of SEQ ID NO:2.

* * * * *

UNITED STATES PATENT AND TRADEMARK OFFICE
CERTIFICATE OF CORRECTION

PATENT NO. : 7,445,788 B2 Page 1 of 1
APPLICATION NO. : 11/503817
DATED : November 4, 2008
INVENTOR(S) : Lawton et al.

It is certified that error appears in the above-identified patent and that said Letters Patent is hereby corrected as shown below:

Title Page 1, item 73 under Assignee "Westbrook, MA" should read --Westbrook, ME--

Signed and Sealed this

Thirtieth Day of December, 2008

JON W. DUDAS
*Director of the United States Patent and Trademark Office*

SEQUENCE LISTING

<160> NUMBER OF SEQ ID NOS: 7

<210> SEQ ID NO 1
<211> LENGTH: 20
<212> TYPE: PRT
<213> ORGANISM: Ehrlichia canis

<400> SEQUENCE: 1

Lys Ser Thr Val Gly Val Phe Gly Leu Lys His Asp Trp Asp Gly Ser
1               5                   10                  15

Pro Ile Leu Lys
            20

<210> SEQ ID NO 2
<211> LENGTH: 20
<212> TYPE: PRT
<213> ORGANISM: Ehrlichia canis

<400> SEQUENCE: 2

Asn Thr Thr Thr Gly Val Phe Gly Leu Lys Gln Asp Trp Asp Gly Ala
1               5                   10                  15

Thr Ile Lys Asp
            20

<210> SEQ ID NO 3
<211> LENGTH: 20
<212> TYPE: PRT
<213> ORGANISM: Ehrlichia chaffeensis

<400> SEQUENCE: 3

Asn Thr Thr Val Gly Val Phe Gly Leu Lys Gln Asn Trp Asp Gly Ser
1               5                   10                  15

Ala Ile Ser Asn
            20

<210> SEQ ID NO 4
<211> LENGTH: 18
<212> TYPE: PRT
<213> ORGANISM: Ehrlichia chaffeensis

```
<400> SEQUENCE: 4

Asn Pro Thr Val Ala Leu Tyr Gly Leu Lys Gln Asp Trp Asn Gly Val
1               5                   10                  15

Ser Ala

<210> SEQ ID NO 5
<211> LENGTH: 19
<212> TYPE: PRT
<213> ORGANISM: Ehrlichia chaffeensis

<400> SEQUENCE: 5

Asn Thr Thr Val Gly Val Phe Gly Ile Glu Gln Asp Trp Asp Arg Cys
1               5                   10                  15

Val Ile Ser

<210> SEQ ID NO 6
<211> LENGTH: 18
<212> TYPE: PRT
<213> ORGANISM: Ehrlichia chaffeensis

<400> SEQUENCE: 6

Asn Pro Thr Val Ala Leu Tyr Gly Leu Lys Gln Asp Trp Glu Gly Ile
1               5                   10                  15

Ser Ser

<210> SEQ ID NO 7
<211> LENGTH: 19
<212> TYPE: PRT
<213> ORGANISM: Ehrlichia chaffeensis

<400> SEQUENCE: 7

Asn Thr Thr Thr Gly Val Phe Gly Leu Lys Gln Asp Trp Asp Gly Ser
1               5                   10                  15

Thr Ile Ser
```